(12) United States Patent
Hashmi et al.

(10) Patent No.: US 8,496,694 B2
(45) Date of Patent: Jul. 30, 2013

(54) VARIABLE ANGLE LOCKING BUTTRESS PINS

(75) Inventors: Adam Hashmi, West Chester, PA (US); Dirk Kerstan, Oberdorf (CH)

(73) Assignee: Depuy Synthes Products, LLC, Raynham, MA (US)

( * ) Notice: Subject to any disclaimer, the term of this patent is extended or adjusted under 35 U.S.C. 154(b) by 225 days.

(21) Appl. No.: 12/947,291

(22) Filed: Nov. 16, 2010

(65) Prior Publication Data
US 2011/0118795 A1    May 19, 2011

Related U.S. Application Data

(60) Provisional application No. 61/261,974, filed on Nov. 17, 2009.

(51) Int. Cl.
*A61B 17/04* (2006.01)
*A61B 17/86* (2006.01)
*A61F 2/08* (2006.01)

(52) U.S. Cl.
USPC ........... 606/315; 606/305; 606/308; 606/309; 606/291

(58) Field of Classification Search
USPC .......................... 606/289, 291, 307, 315–317
See application file for complete search history.

(56) References Cited

U.S. PATENT DOCUMENTS

| | | | |
|---|---|---|---|
| 5,375,956 A * | 12/1994 | Pennig | 411/389 |
| 5,954,722 A * | 9/1999 | Bono | 606/281 |
| 2004/0073218 A1* | 4/2004 | Dahners | 606/69 |
| 2005/0070904 A1* | 3/2005 | Gerlach et al. | 606/69 |
| 2006/0200151 A1 | 9/2006 | Ducharme et al. | |
| 2007/0088360 A1 | 4/2007 | Orbay et al. | |

FOREIGN PATENT DOCUMENTS

| | | |
|---|---|---|
| DE | 4343117 | 6/1995 |
| EP | 1 649 819 | 4/2006 |
| FR | 2 929 102 | 10/2009 |
| WO | 2008/115318 | 9/2008 |
| WO | 2009/023666 | 2/2009 |

* cited by examiner

Primary Examiner — Andrew Yang
(74) Attorney, Agent, or Firm — Fay Kaplun & Marcin, LLP

(57) ABSTRACT

A buttress pin for fixing an implant to a bone, comprises a head at a proximal end, the head comprising a rounded outer profile and including first threading and a shaft extending distally from the head, the shaft including second threading extending over at least a portion of a length thereof, a position of a proximal end of the second threading along the shaft being spaced from a distal end of the first threading by a distance equal to a distance between a proximal end of a hole in an implant to be anchored to a bone via the buttress pin and a surface of the bone when the implant is in a target position on the bone.

18 Claims, 2 Drawing Sheets

VARIABLE ANGLE LOCKING BUTTRESS PINS

PRIORITY CLAIM

The present application claims priority to U.S. Provisional Application Ser. No. 61/261,974 entitled "Variable Angle Locking Buttress Pins" filed on Nov. 17, 2009 to Adam Hashmi and Dirk Kerstan, the entire disclosure of which is incorporated herein by reference.

FIELD OF THE INVENTION

The present invention is directed to the field of bone fixation and, more particularly, to a system and method for the fixation of fractured bones via a buttress pin insertable through a bone fixation device at a selected one of a plurality of angles selected by a physician.

BACKGROUND

Procedures for the fixation of intra-articular and extra-articular bone fracture and osteotomies of the distal radius and other smaller bones have often employed variable angle locking screws with bone plates including correspondingly configured variable angle holes. The combination of a variable angle locking screw with a variable angle hole allows a user to select an angulation of the screw (within a permitted range of angulation) relative to an axis of the hole to, for example, increase a holding strength thereof with the bone. Buttress pins are often used to prevent damage to the bone and surrounding soft tissue and to prevent misalignment of bone fragments during insertion. However, buttress pins have proven difficult to remove from the bone, for example, if it is desired to remove a bone plate after the bone has healed. Specifically, during withdrawal, buttress pins known in the art merely disengage from the plate hole by a minimum distance and then maintain an axial position against the bone and bone plate. Rotation of a driver merely causes these buttress pins to rotate within the bone, preventing a physician from grasping the pin to permit complete withdrawal thereof.

SUMMARY OF THE INVENTION

The present invention is directed to a buttress pin for fixing an implant to a bone, comprising a head at a proximal end, the head comprising a rounded outer profile and including first threading and a shaft extending distally from the head, the shaft including second threading extending over at least a portion of a length thereof, a position of a distal end of the second threading along the shaft being spaced from a distal end of the first threading by a distance equal to a distance between a proximal end of a hole in an implant to be anchored to a bone via the buttress pin and a surface of the bone when the implant is in a target position on the bone.

DETAILED DESCRIPTION

Figure 1:
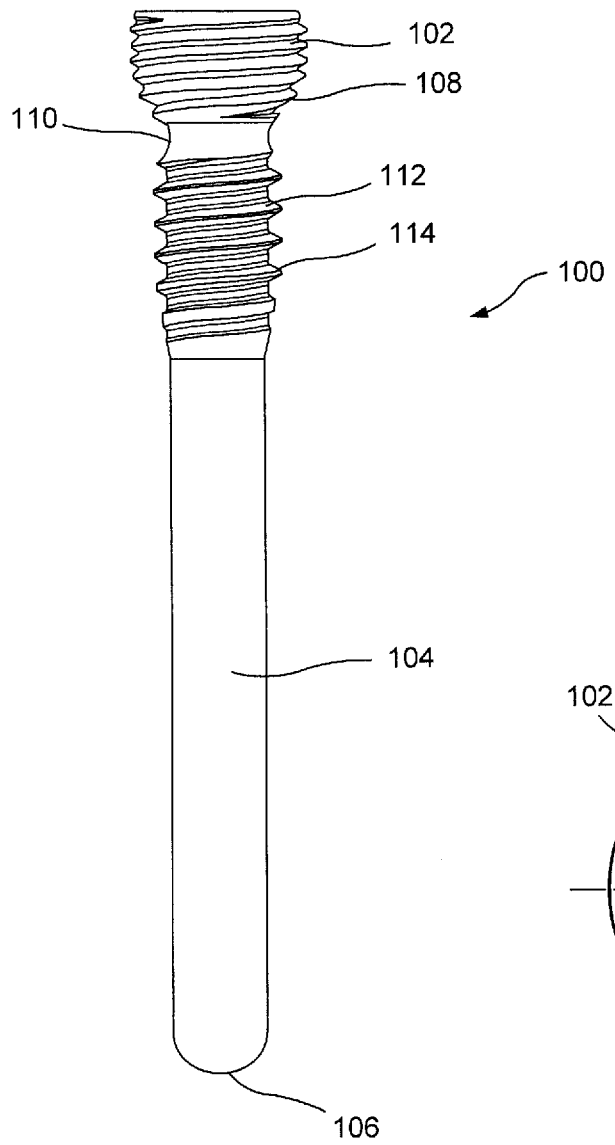
FIG. 1 shows a perspective view of a system according to a first exemplary embodiment of the present invention.

The present invention may be further understood with reference to the following description and the appended drawings, wherein like elements are referred to with the same reference numerals. The exemplary embodiments of the present invention relate to a system and method for the fixation of complex intra- and extra-articular bone fractures as well as osteotomies of the distal radius and other small bones of a body. The exemplary system and method of the present invention may also be used to strengthen poor quality bone such as, for example, osteoporotic bone, where screw purchase may be compromised. An exemplary bone fixation buttress pin according to the present invention comprises a threaded head and a shaft having a smooth distal portion and a rounded distal end configured to minimize trauma to soft tissue as the buttress pin is inserted into a target bone while preventing displacement of bone fragments. To facilitate removal from the bone, the bone fixation buttress pin according to the present invention includes a threaded neck at a proximal end of the shaft extending to a distal end of the head. As will be described in greater detail hereinafter, the threading on the neck is positioned so that, as the buttress pin is being inserted through a bone plate hole into a bone, threading on the head of the buttress pin first engages the hole of the bone plate at approximately the same time that a distal-most end of the thread of the neck first engages the bone without causing a compression of the bone plate to the bone. In an exemplary embodiment, the buttress pin of the present invention is used for the fixation of the distal radius or other small bones of the body. However, it will be understood by those of skill in the art that the buttress pin of the present invention may be used for the fixation of any type of bone in the body.

Figure 2:
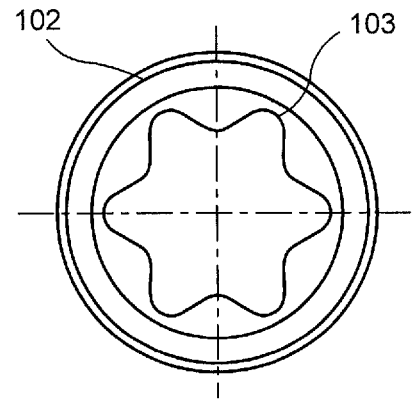
FIG. 2 shows a top view of the system of FIG. 1.

As shown in FIGS. 1-2, a buttress pin 100 according to a first exemplary embodiment of the present invention comprises a head 102 and a shaft 104 extending distally therefrom to a rounded distal end 106. The buttress pin 100 according to this exemplary embodiment is formed of 316L stainless steel or titanium. Nevertheless, as those skilled in the art will understand, buttress pins according to the present invention may be formed of any suitable material. The head 102 includes threading 108 around a surface thereof configured to lockingly engage a corresponding threading formed on a hole extending through a bone implant (e.g., a bone plate, not shown). The threading 108 according to this embodiment is a double-lead threading configured to engage double-lead threading of a bone plate hole (not shown). However, those skilled in the art will understand that single-lead threading may be used if desired. That is, a buttress pin according to this invention will preferably be used in conjunction with a bone fixation device (e.g., bone plate) having a hole configured to lockingly engage the head of the buttress pin. A proximal face of the head 102 comprises a driver engagement recess 103 configured to permit engagement of the buttress pin 100 with a driver (not shown) as would be understood by those skilled in the art. It is noted that although the driver engagement recess 103 is shown having a star-shaped cross-section, the driver engagement recess 103 may have any other shape, including slotted, crosshead, square, hexagonal or any other shape configured to engage a respectively shaped driver (not shown). In an exemplary embodiment, the recess 103 may extend into the head 102 by a predetermined distance sufficient to permit a secure engagement with the driver. The head 102 is formed with a rounded outer wall having a substantially spherical outer profile. It is noted, however, that a conical outer profile of the head may also be employed without deviating from the spirit and scope of the present invention. In an exemplary embodiment, a longitudinal length of the head 102 ranges from approximately 1.7-2.34 mm. although any other length may be employed to accommodate insertion of the head 102 into a hole extending through the bone implant (not shown) so that, when mounted in the bone as desired the head 102 does not project proximally beyond a proximal surface of a bone plate (i.e., a surface facing away from the bone) through which it is inserted.

A distal end of the head 102 is connected to the shaft 104 via a rounded connection opening to a smooth non-threaded section 110 extending from the proximal end of the shaft 104 to the distal end of a threaded portion 112 of the shaft 104. It is noted, however, that the non-threaded section 110 may also be provided with threads without deviating from the scope of the present invention. The length of the threaded portion 112 is selected based on an average distance between a bottom surface of the bone plate (not shown) contacting the bone and the near cortex of the bone. The non-threaded section 110 may be formed of any suitable length and outer diameter. The threaded portion 112 includes threading 114 extending over a portion of the length of the shaft 104. A distal end of the threading 114 is preferably positioned so that, the threading 114 first engages the bone at approximately the same time that the distal end of the threading 108 first engages the threading of the hole in the bone plate through which it is being inserted. The threading 114 according to this embodiment is a single lead threading corresponding to the threading formed on traditional cortical screws. Those skilled in the art will understand that although the head 102 comprises double-lead threading 108 and the threading 114 is single-lead threading, each of these threaded portions 108, 114 will turn at the same speed since the thread profile of the head 102 is approximately half of that of the threading 114. The pitches of the threadings 108 and 114 are preferably equal to one another so that, as the pin 100 is driven into the bone and engaged with the hole of the bone plate, the bone plate is not reduced relative to the bone—i.e., so that the axial travel of the head 102 relative to the bone plate per revolution of the pin 100 is equal to the axial travel of the shaft 104 relative to the bone per revolution. In a pin according to an alternate embodiment (not shown) of the invention, the threads 114 of the threaded portion 112 may be formed with a variable pitch to permit the threads 114 to be sharper and cut into the bone (not shown) more easily. In such an embodiment, a diameter of the threaded portion 112 of the shaft 104 remains substantially constant along an axial length thereof.

An outer diameter of the threading 114 of the pin 100 shown in FIGS. 1-2 decreases from a diameter of approximately 2.4 mm at a proximal end to a second diameter of approximately 1.8 mm at a distal end along a taper angle of approximately 10°. The taper of the threading 114 aids in starting threads in the target bone since the exemplary threading 114 does not comprise any cutting flutes, as those skilled in the art will understand. It is further noted that any diameter and taper angle of the threaded portion 112 may be employed without deviating from the scope of the present invention. Furthermore, in an exemplary embodiment of the present invention, the threaded portion 112 has a longitudinal length of approximately 4 mm. Those skilled in the art will understand that this length may be changed based on the dimensions of a bone implant to be employed with the pin and the spatial relationship of the bone implant with the bone. Specifically, in a preferred embodiment, a distal end of the threading 114 is configured to engage the bone at approximately the same time that the threading 108 come into contact with the bone implant. Thus the threaded portion 112 is preferably positioned and dimensioned so that, when the distal end of the threading 108 is seated at the proximal end of a bone plate hole through which the pin 100 will be inserted, the distal end of the threaded portion 112 contacts the outer surface of the bone. If the bone implant is configured to lie flush against the bone and has a thickness of approximately 4 mm, the distal end of the threaded portion 112 will be positioned 4 mm. distal of the distal end of the threading 108. Those skilled in the art will understand that the threaded portion 112 therefore permits the buttress pin 100 to be unscrewed from the bone by a distance sufficient to permit a physician to grip the head 102 to withdraw the buttress pin 100 from the bone. Specifically, the threaded portion 112 is configured to engage the bone (not shown) while the head 102 is still separated from the target bone plate (not shown) by approximately one turn of the threading 114. Thus, the threaded portion 112 permits a user to grip the head 102 with a pair of forceps to aid in removal from the bone without significantly complicating the removal procedure. As those skilled in the art will understand, the forceps may be formed with serrated gripping portions to aid in gripping of the head 102.

In accordance with an exemplary method, an exemplary bone implant (e.g., a dorsal distal radius plate) is positioned over a target portion of a fractured, osteoporotic or otherwise weakened bone such as a distal radius (not shown). A variable angle locking drill guide is then screwed through a target plate hole (not shown) and into the bone. As those skilled in the art will understand, the drill guide and plate hole are formed with dimensions suited for receipt of the buttress pin 100 therethrough. In the embodiment discussed, the drill guide may be a 1.8 mm. drill guide. The drill guide is inserted into the bone at a desired angle selected to suit the requirements of the procedure being performed. A drill bit is then used to drill bi-cortically through the bone. It is noted, however, that the drill bit may optionally extend through a uni-cortical portion of the bone if so desired. The drill guide is then removed from the bone using a technique known in the art. The buttress pin 100 is then positioned through the plate hole (not shown) and into the bone (not shown) using the pre-drilled hole as a guide. Specifically, the buttress pin 100 is manually pushed into the bone until the threads 114 come into contact with the bone. The physician or other user then uses a driver to screwably insert the buttress pin 100 into the bone until the head 102 is firmly seated in the bone implant hole. The rounded distal end 106 of the buttress pin 106 permits the physician to insert the buttress pin 100 through the implant and into the bone while minimizing damage to surrounding soft tissue. Furthermore, the tapered shape of the head 102 and the threading 108 are configured to correspond to an interior shape of a variable angle locking hole in a bone implant so that the buttress pin 100 may be inserted therethrough at any desired angle within a range of ±15° from a central axis of the hole, as those skilled in the art will understand. As those skilled in the art will understand, a bone plate or other implant may be anchored to one or more desired portions of bone using any number of buttress pins 100 alone or in combination with any number of other bone fixation screws and/or pins. Furthermore, in a preferred embodiment, the exemplary buttress pins 100 according to the present invention may be used in a head of the distal radius plate although any other positions may be employed without deviating from the spirit and scope of the present invention.

Figure 3:
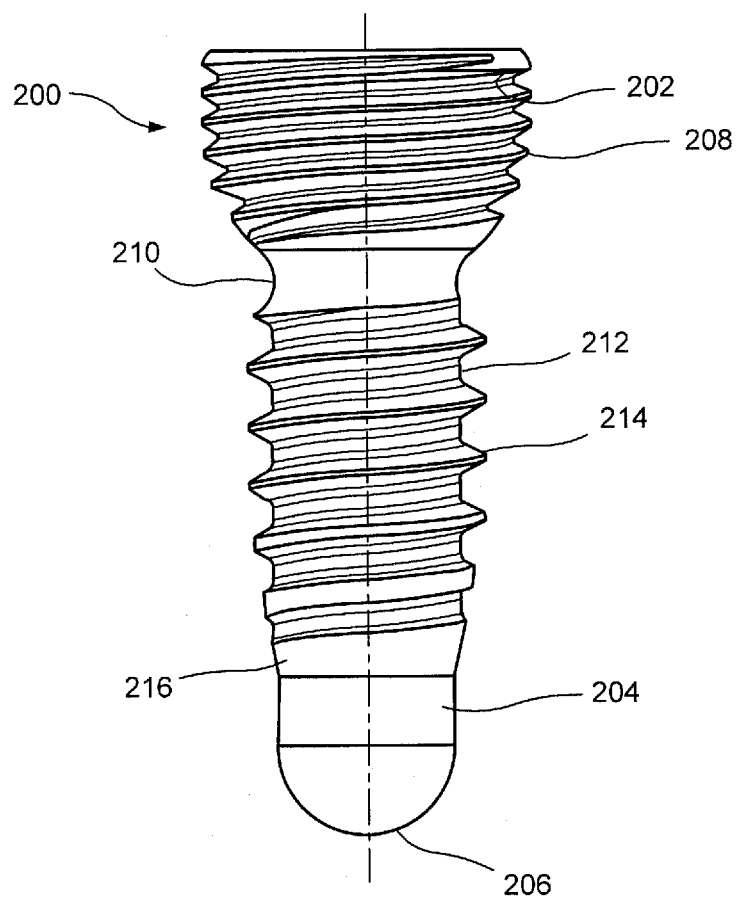
FIG. 3 shows a perspective view of a system according to a second exemplary embodiment of the present invention.

As shown in FIG. 3, a buttress pin 200 according to an alternate embodiment of the invention is formed substantially similarly to the buttress pin 100 of FIG. 1 except that a length of a shaft 204 is shorter than the length of the shaft 104. In an exemplary embodiment, a length of the threaded portion 212 remains substantially constant irrespective of a length of the shaft 204, which may range in length from 8 mm to 30 mm depending on the dimensions of a target bone. A pitch of the threading 208 on the head 202 of the buttress pin 200 may be the same as a pitch of the threads 214 of the threaded portion 212 of the shaft 204 so that, as the pin 200 is driven into the bone and engaged with the hole of the bone plate, the bone plate is not reduced relative to the bone, as described in greater detail earlier with respect to FIGS. 1-2. In another embodiment of the invention, the pitch of the threading 208 may be less than the pitch of the threads 214 so that as the pin 200 is rotated into the bone and the head 202 is rotated into the bone plate, the bone and the bone plate a drawn toward one another compressing the bone plate against the bone. A distal portion of the shaft 204 further comprises a non-threaded tapered portion 216 which tapers down to a reduced diameter at a distal end 206 of the buttress pin 200. The threaded portion 212 is formed with a taper substantially similar to the taper of the threaded portion 112, as described in greater detail earlier.

The head 202 of the buttress pin 200 is also formed with a substantially spherical outer profile to permit engagement with a rounded plate hole. In another embodiment, the outer profile of the head 202 may be substantially conical to permit insertion into a respectively shaped plate hole, as those skilled in the art will understand. As those skilled in the art will understand, the substantially conical hole may comprise other features to permit angulation of the buttress pin 100 therewithin.

It will be understood by those of skill in the art that the buttress implants 100, 200 may be provided with any of a plurality of other features without deviating from the scope of the present invention. Specifically, the shafts 104, 204 may be provided with any plurality of cutting flutes to aid in insertion thereof into the bone. The rounded distal ends 106, 206 may alternately also be formed of any other blunted shape (e.g., square, etc.). Furthermore, the exemplary buttress pins 100 of the present invention may be employed with any variable angle locking compression plate ("LCP") hole extending through the plate or through a locking hole of a plate if inserted along a hole axis of the locking hole. Furthermore, it is noted that although the exemplary system and method of the present invention is directed to variable angle locking pins, non-variable angle locking pins may also be employed without deviating from the spirit and scope of the present invention.

It will be apparent to those skilled in the art that various modifications and variations can be made in the structure and the methodology of the present invention, without departing from the spirit or the scope of the invention. Thus, it is intended that the present invention cover the modifications and variations of this invention provided that they come within the scope of the appended claims and their equivalents.

What is claimed is:

1. A buttress pin for fixing an implant to a bone, comprising:
   a head at a proximal end, the head comprising an outer profile rounded in a longitudinal direction and including first threading; and
   a shaft extending distally from the head, the shaft including a first portion including second threading extending thereover, a position of a proximal end of the second threading along the shaft being spaced from a distal end of the first threading by a distance corresponding to a distance between a proximal end of a hole in an implant to be anchored to a bone via the buttress pin and a surface of the bone when the implant is in a target position on the bone, the shaft further comprising a second cylindrical portion extending from the first portion to a third portion of the buttress pin, the second portion being unthreaded, the third portion being blunted.

2. The device of claim 1, wherein a pitch of the first threading is the same as a pitch of the second threading.

3. The device of claim 1, wherein the first threading is double-lead threading.

4. The device of claim 1, wherein the second threading is single-lead threading.

5. The device of claim 1, wherein the second threading is tapered so that a diameter of the second threading at a proximal end thereof is greater than a diameter at a distal end thereof.

6. The device of claim 5, wherein the taper angle is approximately 10 degrees.

7. The device of claim 1, wherein an outer profile of the head is configured to correspond to a variable angle locking hole into which it is to be inserted to permit insertion thereof through the variable angle locking hole at any angle within a permitted range of angulation.

8. The device of claim 7, wherein the head is configured to permit insertion of the pin through a variable angle locking hole within a range of angulation of ±15°.

9. The device of claim 1, wherein the distal end of the shaft is rounded.

10. The device of claim 1, wherein a pitch of the first threading is smaller than a pitch of the second threading.

11. The device of claim 10, wherein a pitch of the second threading varies along a length thereof.

12. The device of claim 1, further comprising a non-threaded section between the first and second threadings.

13. The device of claim 1, further comprising a driver recess on a proximal face of the head configured to permit engagement with a driving mechanism.

14. The device of claim 1, wherein an outer profile of the head is one of spherical and conical.

15. A method of fixing an implant to a bone, comprising:
   axially inserting a shaft of a buttress pin through a hole of a bone implant and into a target portion of a bone until a first threading of a head of the pin engages a corresponding threading of the hole, the pin including a shaft extending distally from the head and including a first portion with a second threading extending therealong, a proximal end of the second threading being spaced from a distal end of the first threading by a distance corresponding to a distance between a proximal end of the hole and a surface of the bone, the shaft further comprising a second cylindrical portion extending from the first portion to a third portion of the buttress pin, the second portion being unthreaded, the third portion being blunted; and
   rotating the pin to threadedly drive the neck into the bone and to threadedly engage the head with the hole.

16. The method of claim 15, further comprising the step of pre-drilling a bore into the bone prior to the insertion of the buttress pin thereinto.

17. The device of claim 1, wherein the distal end of the shaft is square.

18. The device of claim 1, wherein the second portion tapers down to a reduced diameter toward the distal end of the shaft.

* * * * *